(12) United States Patent  
Reichwein

(10) Patent No.: US 9,572,260 B2  
(45) Date of Patent: Feb. 14, 2017

(54) DEVICE FOR STORING ELECTROMAGNETIC ENERGY FROM BIOLOGICAL SOURCE

(71) Applicant: Dietrich Reichwein, Schärding (AT)

(72) Inventor: Dietrich Reichwein, Schärding (AT)

(\*) Notice: Subject to any disclaimer, the term of this patent is extended or adjusted under 35 U.S.C. 154(b) by 211 days.

(21) Appl. No.: 14/170,966

(22) Filed: Feb. 3, 2014

(65) Prior Publication Data

US 2014/0251665 A1    Sep. 11, 2014

Related U.S. Application Data

(63) Continuation-in-part of application No. PCT/EP2012/065268, filed on Aug. 3, 2012.

(30) Foreign Application Priority Data

Aug. 3, 2011    (DE) .................... 10 2011 109 338

(51) Int. Cl.
```
H05K 1/18      (2006.01)
H05K 1/03      (2006.01)
H05K 1/09      (2006.01)
G01N 33/487    (2006.01)
```
(52) U.S. Cl.  
CPC ........ *H05K 1/183* (2013.01); *G01N 33/48735* (2013.01); *H05K 1/0306* (2013.01); *H05K 1/09* (2013.01)

(58) Field of Classification Search  
None  
See application file for complete search history.

(56) References Cited

U.S. PATENT DOCUMENTS

| | | | | |
|---|---|---|---|---|
| 3,979,184 A * | 9/1976 | Giaever | ................ | G01N 21/45 204/192.22 |
| 4,803,450 A * | 2/1989 | Burgess | ................. | H01P 3/088 228/180.22 |
| 5,386,339 A * | 1/1995 | Polinski, Sr. | ....... | H01L 23/3735 174/252 |
| 5,435,970 A * | 7/1995 | Mamenta | ............. | G01N 33/491 422/408 |
| 5,656,503 A * | 8/1997 | May | ................. | G01N 33/54386 427/2.11 |
| 5,731,067 A * | 3/1998 | Asai | .................... | H01L 23/3677 174/252 |
| 6,254,827 B1 * | 7/2001 | Ackley | ................ | B01J 19/0046 257/E21.43 |

(Continued)

FOREIGN PATENT DOCUMENTS

DE    3938238 A1    5/1991  
DE    44 47 328 A1    7/1996  
(Continued)

*Primary Examiner* — Chau N Nguyen  
*Assistant Examiner* — Muhammed Azam  
(74) *Attorney, Agent, or Firm* — Brinks Gilson & Lione

(57) ABSTRACT

A device having a planar substrate, the substrate having a first side and a second side, where at least one first arrangement may be provided on the first side, which has at least one first single-wire and possibly at least one first cavity, and where at least one first device for storing electromagnetic energy is provided, one end of a single-wire being connected to the device for storing the electromagnetic energy, and the other end of the single-wire being disposed possibly, as free end, in, below or abutting on the first cavity.

47 Claims, 6 Drawing Sheets

(56) References Cited

U.S. PATENT DOCUMENTS

| | | | | |
|---|---|---|---|---|
| 6,659,355 B1* | 12/2003 | Fischer | G06K 19/07722 | 235/451 |
| 6,875,921 B1* | 4/2005 | Conn | H01L 23/50 | 174/534 |
| 7,035,080 B1* | 4/2006 | Devoe | H05K 1/0231 | 361/303 |
| 7,556,723 B2* | 7/2009 | Funke | G01N 27/3272 | 204/403.02 |
| 7,638,866 B1* | 12/2009 | Bean | H01L 23/57 | 257/686 |
| 2001/0006457 A1* | 7/2001 | Fujino | H05K 1/0231 | 361/761 |
| 2001/0019292 A1* | 9/2001 | Funahara | H05K 1/181 | 331/68 |
| 2001/0024148 A1* | 9/2001 | Gerstenberg | H05K 1/0216 | 333/185 |
| 2001/0054481 A1* | 12/2001 | Harada | B32B 38/10 | 156/289 |
| 2001/0055800 A1* | 12/2001 | Bara | B01L 3/5085 | 435/287.1 |
| 2002/0011907 A1* | 1/2002 | Yamada | H01L 23/5385 | 333/204 |
| 2002/0039667 A1* | 4/2002 | Takaya | H01B 3/004 | 428/824 |
| 2002/0041827 A1* | 4/2002 | Yager | G01N 30/0005 | 422/400 |
| 2002/0072084 A1* | 6/2002 | Meserol | G01N 27/3272 | 435/26 |
| 2002/0084103 A1* | 7/2002 | Komatsu | C04B 35/584 | 174/255 |
| 2002/0084104 A1* | 7/2002 | Sasaki | H01L 23/49822 | 174/255 |
| 2002/0085360 A1* | 7/2002 | Doi | H05K 1/16 | 361/782 |
| 2002/0106577 A1* | 8/2002 | Kubota | G03F 7/0047 | 430/252 |
| 2002/0118523 A1* | 8/2002 | Okabe | H01L 21/4857 | 361/793 |
| 2002/0197622 A1* | 12/2002 | McDevitt | G01N 33/54373 | 435/6.12 |
| 2003/0028170 A1* | 2/2003 | Anderson | A61N 1/0436 | 604/501 |
| 2003/0030533 A1* | 2/2003 | Waffenschmidt | H05K 1/165 | 336/200 |
| 2003/0032196 A1* | 2/2003 | Zhou | G01N 33/525 | 436/169 |
| 2003/0042150 A1 | 3/2003 | Ryu et al. | | |
| 2003/0207442 A1* | 11/2003 | Markovsky | A23D 9/00 | 435/287.2 |
| 2004/0012085 A1* | 1/2004 | Shioga | H01L 23/3107 | 257/723 |
| 2004/0017670 A1* | 1/2004 | Bando | H01L 23/13 | 361/761 |
| 2004/0043479 A1* | 3/2004 | Briscoe | B01L 3/5025 | 435/288.5 |
| 2004/0067577 A1* | 4/2004 | Wilson | B01L 3/5027 | 435/283.1 |
| 2004/0070919 A1* | 4/2004 | Takeuchi | H01G 4/012 | 361/321.2 |
| 2004/0072739 A1* | 4/2004 | Anderson | C12N 15/62 | 514/100 |
| 2004/0081581 A1* | 4/2004 | Mount | G01N 21/29 | 422/400 |
| 2004/0101439 A1* | 5/2004 | Fusco | B01J 19/0046 | 506/33 |
| 2004/0115831 A1* | 6/2004 | Meathrel | G01N 33/558 | 436/514 |
| 2004/0222480 A1* | 11/2004 | Weisbuch | G01N 21/7703 | 257/433 |
| 2005/0004442 A1* | 1/2005 | Ozaki | G01N 33/48707 | 600/407 |
| 2005/0064732 A1* | 3/2005 | Muench | H01L 23/057 | 439/55 |
| 2005/0196746 A1* | 9/2005 | Xu | G01N 33/48728 | 435/4 |
| 2005/0196747 A1* | 9/2005 | Stiene | B01L 3/502792 | 435/4 |
| 2005/0266478 A1* | 12/2005 | Huang | G01N 33/48728 | 435/6.11 |
| 2006/0057771 A1* | 3/2006 | Kovacs | G01N 33/4836 | 438/106 |
| 2006/0065361 A1* | 3/2006 | Stiene | B01L 3/502707 | 156/292 |
| 2006/0152334 A1* | 7/2006 | Maercklein | H01C 7/003 | 338/210 |
| 2006/0181485 A1* | 8/2006 | Kim | H05B 33/0812 | 345/46 |
| 2006/0182654 A1* | 8/2006 | Cumberland | G01N 21/78 | 422/400 |
| 2006/0215380 A1* | 9/2006 | Lu | H01G 4/232 | 361/763 |
| 2006/0234209 A1* | 10/2006 | Walker | G01N 33/537 | 435/5 |
| 2006/0252054 A1* | 11/2006 | Lin | A61M 1/36 | 435/6.11 |
| 2006/0280918 A1* | 12/2006 | Murata | H05K 1/09 | 428/209 |
| 2007/0015175 A1* | 1/2007 | Kumar | G01N 33/56983 | 435/6.11 |
| 2007/0048746 A1* | 3/2007 | Su | B82Y 15/00 | 435/6.11 |
| 2007/0072287 A1* | 3/2007 | Morisette | B01L 3/502715 | 435/287.2 |
| 2007/0086145 A1* | 4/2007 | Kubota | H01L 23/49822 | 361/311 |
| 2007/0102777 A1* | 5/2007 | Davuluri | H01S 5/02252 | 257/432 |
| 2007/0123759 A1* | 5/2007 | Grata | A61B 5/1112 | 600/310 |
| 2007/0269901 A1* | 11/2007 | Armani | G01N 21/7746 | 436/172 |
| 2008/0000061 A1* | 1/2008 | Jeong | H01G 4/232 | 29/25.41 |
| 2008/0158777 A1* | 7/2008 | Sohn | H01G 4/232 | 361/321.1 |
| 2008/0283488 A1* | 11/2008 | Brunner | H05K 3/181 | 216/13 |
| 2009/0000957 A1* | 1/2009 | Dubin | B01J 19/0046 | 205/701 |
| 2009/0002700 A1* | 1/2009 | Wang | G01N 21/658 | 356/301 |
| 2009/0221011 A1* | 9/2009 | Stiene | B01L 3/502715 | 435/13 |
| 2010/0068822 A1* | 3/2010 | Heydenhauss | B01L 3/50273 | 436/172 |
| 2010/0208955 A1* | 8/2010 | Mehes | G01N 21/6452 | 382/128 |
| 2010/0328845 A1* | 12/2010 | Hiralal | H01G 11/36 | 361/502 |
| 2011/0209966 A1* | 9/2011 | Graef | G06Q 40/00 | 194/302 |
| 2011/0214906 A1* | 9/2011 | Baars | B05D 5/12 | 174/257 |
| 2012/0022431 A1* | 1/2012 | Krinke | A61N 1/0428 | 604/20 |
| 2014/0322103 A1* | 10/2014 | McDevitt | B01L 3/5027 | 422/554 |

FOREIGN PATENT DOCUMENTS

| | | |
|---|---|---|
| DE | 601 06 228 T2 | 10/2005 |
| JP | 2004241497 A | 8/2004 |
| WO | WO0134096 A1 | 5/2001 |

* cited by examiner

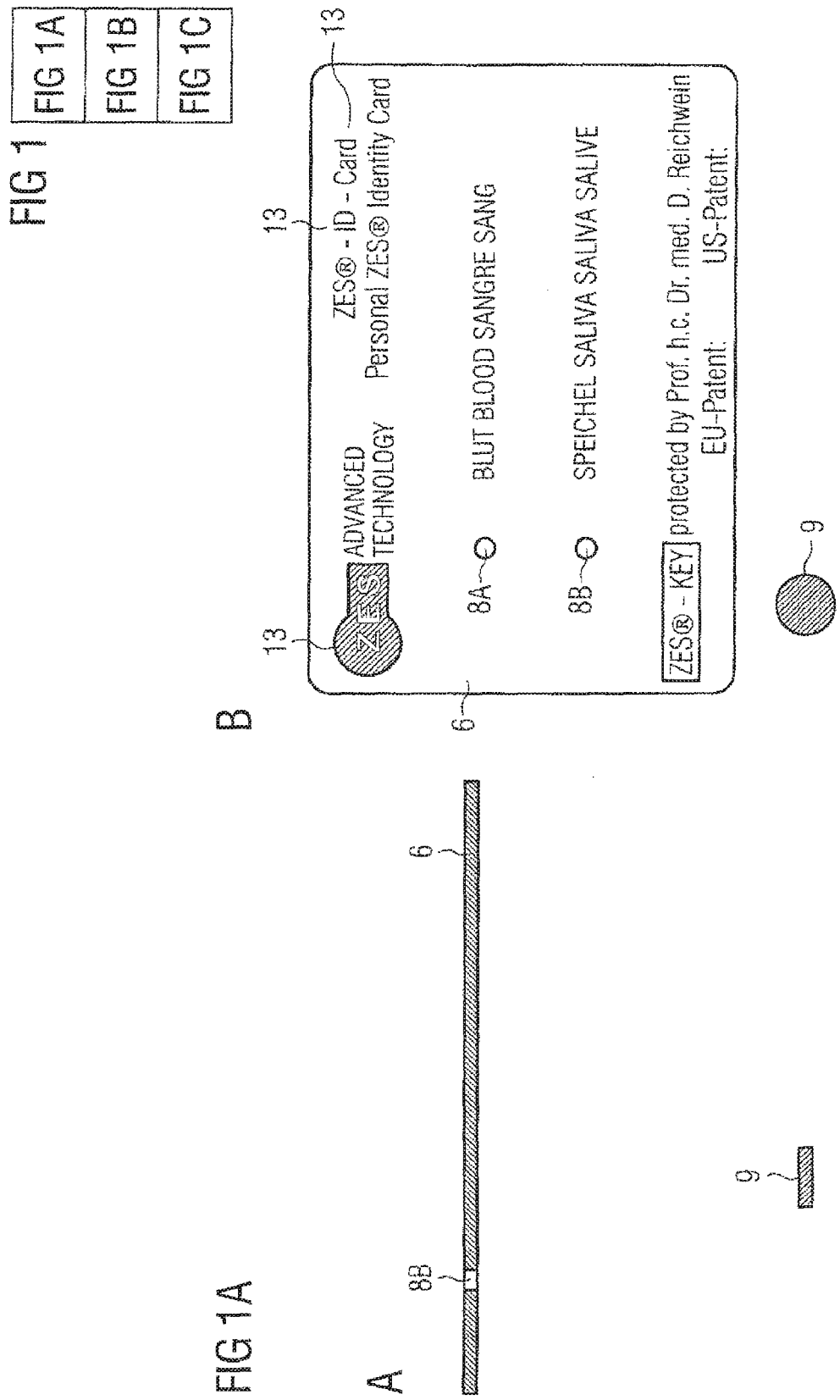

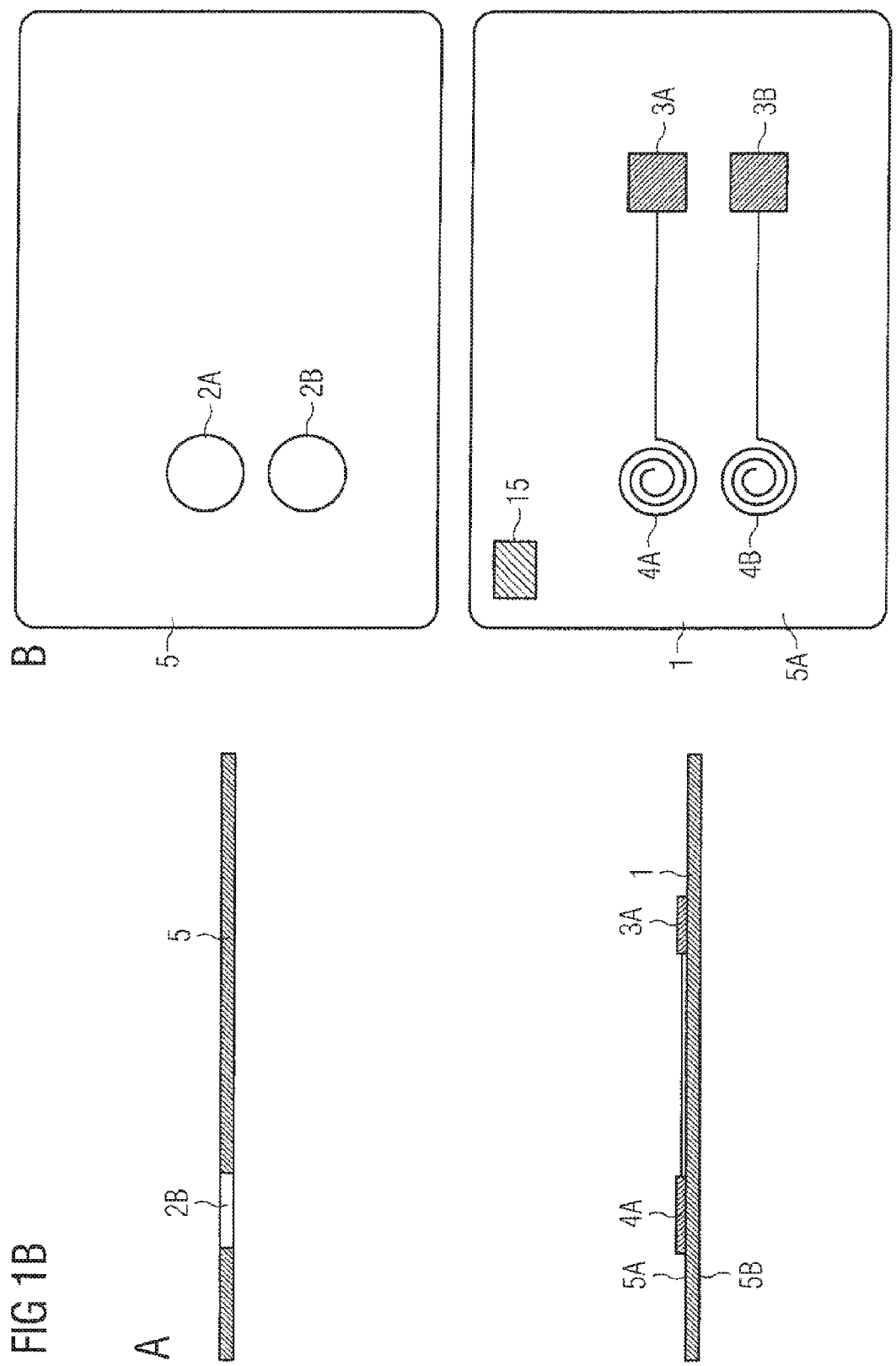

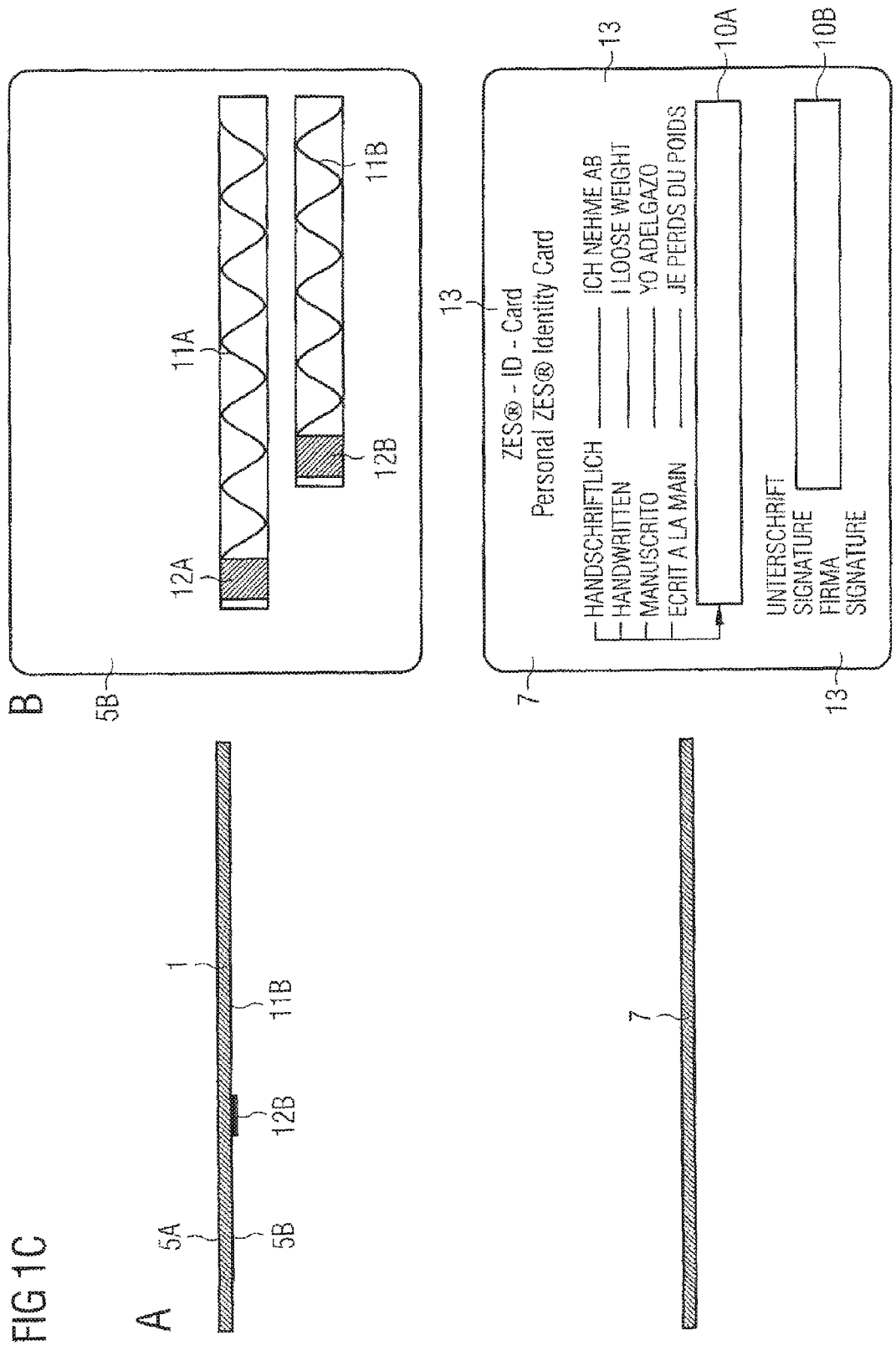

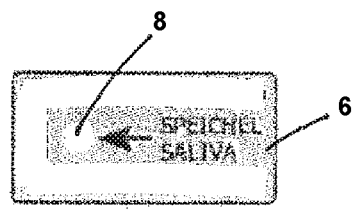
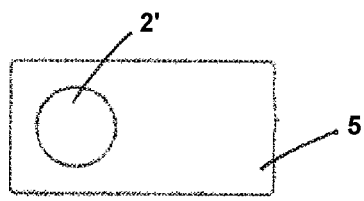
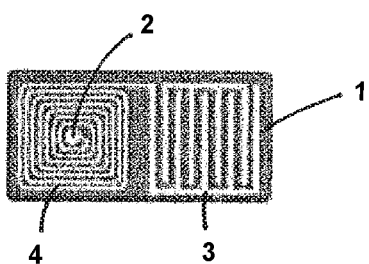
FIG 3

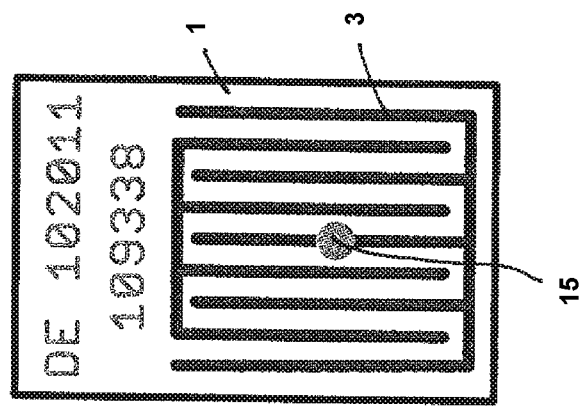
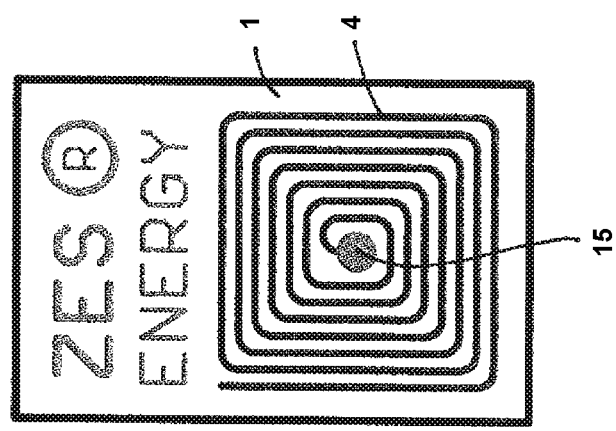
FIG 4

DEVICE FOR STORING ELECTROMAGNETIC ENERGY FROM BIOLOGICAL SOURCE

CROSS-REFERENCE TO RELATED APPLICATIONS

This application is a continuation-in-part of PCT/EP2012/065268, filed Aug. 3, 2012, which in turn claims benefit of German patent application DE 10 2011 109 338.2 filed Aug. 3, 2011.

BACKGROUND

The present invention relates to a device for storing electromagnetic energy and signals, for example from biological systems. The device can pick up electrical signals and, possibly modified, emit them again.

Detection of biological processes which go back to moving electrical charges is known from the state of the art (e.g. in medicine in the case of EEG, ECG and/or ENG). Furthermore, it is known that biological processes can be influenced by means of electromagnetic devices (e.g. biophoton spectral analysis, biological resonance techniques, the use of magnetic fields for faster germination or for acceleration of vital processes).

Within living cells, electrical potential variations can occur due to de-, re- or hyperpolarisation of the cell membrane. These electrical potential variations generate an electromagnetic field or effect emission of electromagnetic waves.

Biological cells consist of a large number of charged molecules, such as for example charged proteins, nucleic acids, lipids and carbohydrates. In the cell, a high concentration of molecules (approx. 200-400 mg/ml for proteins) prevails and the molecules are found in constant motion. Without the movement of the molecules, the cell would not be viable.

It is known that moving electrical charges produce electromagnetic radiation, i.e. electromagnetic waves. Since a large number of cellular molecules is permanently in motion (driven passively by Brownian molecular motion and actively by energy, e.g. by ATP hydrolysis), living cells permanently emit—even if weak—electromagnetic radiation.

It is the object of the present invention to provide a device which can absorb and store electromagnetic signals of biological systems and can also emit electromagnetic signals to biological systems.

SUMMARY

The device according to the invention has a substrate, advantageously having at least two layers, and also having a first side and a second side, characterised in that, on the first side, at least one first arrangement is provided, which has at least one first single-wire and in that, on the first side or on the second side of the substrate, at least one first device for storing electromagnetic, in particular electrical, energy (advantageously a capacitor) is provided, one end of the single-wire being connected electrically conductively to the device for storing the electromagnetic energy. Possibly, the first arrangement can advantageously have at least one cavity, the second end of the single-wire being disposed advantageously as free end in, below or abutting on the cavity.

Fundamental to the present invention is the knowledge that biological systems, such as living cells, represent a dense collection of emitters of electromagnetic signals, e.g. in the form of electromagnetic radiation.

Cells in a cell composite, such as for example the human organism, can have different cellular activities (e.g. different metabolic activities). A variably strong emission of different electromagnetic waves which can be cell type- and/or tissue type-specific result in turn therefrom. Furthermore, the electromagnetic signals which are emitted by cells depend upon their state. Consequently, an emission of electromagnetic radiation which depends upon many parameters, such as for example cell type and momentary state of a cell, are therefore produced.

The device according to the invention makes it possible to absorb this electromagnetic radiation of biological origin, to store it and to emit corresponding electromagnetic radiation or signals. In principle, it is therefore also possible to feed back biological signals into biological systems with the device according to the invention and, by means of specific alteration of the signals, to engage in a compensating manner in the respective biological system.

Preferably, a first layer is configured as circuit board, on or in which the single-wire and/or the device for storing electromagnetic energy, in particular as strip conductors, are configured.

For particular preference, the first layer comprises
a) an electrically insulating material as basic material, preferably selected from the group consisting of epoxy resin, glass fibre, paper, ceramic, aluminium oxide, polyimide, polytetrafluoroethylene and polyethylene; and
b) an electrically conductive material as conductive material, preferably a metal, particularly preferred copper, tin, nickel, gold and/or platinum.

A second layer of the device according to the invention can be configured as a self-adhesive spacer which comprises a through-opening, the second layer contacting the first layer such that the through-opening is situated above the free end of the single-wire and forms a cavity. A biological sample, for example a body fluid, can be introduced into this cavity.

The second layer preferably comprises plastic material, preferably polycarbonate, polyethylene or polyvinyl chloride, or consists thereof.

The through-opening in the second layer can be circular and have a diameter of 4.0-15.0 mm, preferably 6.0-12.0 mm, particularly preferred 8.0-9.0 mm. Alternatively, the through-opening can be angular or oval.

The through-opening of the second layer preferably comprises an absorbent material. The absorbent material can hereby be configured as a circular, absorbent pad, preferably with a diameter of 4.0-15.0 mm, preferably 6.0-12.0 mm, particularly preferred 8.0-9.0 mm. In a preferred embodiment, the absorbent material (e.g. a circular, absorbent pad) is configured such that it absorbs body fluids, preferably blood, saliva, cells, cell lysate, in particular samples comprising DNA.

Optionally, the device according to the invention can have a third layer which is configured as a self-adhesive decorative foil and comprises a through-opening, the through-opening of the third layer being preferably situated in the centre above the through-opening of the second layer.

This third layer can comprise plastic material, preferably polycarbonate, polyethylene or polyvinyl chloride, or consist thereof.

The through-opening of the third layer can have a circular configuration and have a diameter of 0.5-3.5 mm, preferably 1.0-3.0 mm, particularly preferred 1.5-2.5 mm. Alternatively, the through-opening of the third layer can be oval or rectangular.

In a preferred embodiment of the device according to the invention, on the second side of the substrate, advantageously on the second side of the first layer, at least one second arrangement is provided, which second arrangement has at least one field and at least one second single-wire and at least one second device for storing electrical energy is provided, one end of the second single-wire being connected electrically conductively to the second device for storing electromagnetic energy and the other end being disposed as free end in, on or abutting on the field.

Optionally, the device has a fourth layer which is disposed on the second side of the first layer or of the third layer, which fourth layer is configured as a self-adhesive decorative foil and has at least one field or at least one through-cavity in the form of a field.

The fourth layer can comprise plastic material, preferably polycarbonate, polyethylene or polyvinyl chloride, or consist thereof.

The field or the through-cavity in the form of a field can be rectangular, preferably the dimensions have length×width of 2-7 cm×0.5-2 cm, particularly preferred of 4-6 cm×0.8-1.5 cm. Alternatively, the field or the through-cavity in the form of a field can be circular or oval.

The field or the at least one cavity in the form of a field preferably has a material which can be written upon. The material which can be written upon can be configured such that it adsorbs and/or absorbs solid and/or liquid writing material.

The at least two layers of the substrate of the device (e.g. the first, second, third and fourth layer) can be respectively planar, cuboid or cylindrical, in particular rectangular.

The substrate is configured preferably in card format and preferably has dimensions in length×width×height of 2-14 cm×2-10 cm×0.05-0.60 mm, particularly preferred of 8-9 cm×5-6 cm×0.15-0.40 mm.

Furthermore, the substrate can have at least one further third device for storing electromagnetic energy which is available for storing electromagnetic energy or signals from outside.

At least one, several or all of the stores for electromagnetic energy are preferably a capacitor or have a capacitor.

The device according to the invention can comprise one, two or three first arrangements on the first side. On the second side, the device can have one, two or three second arrangements.

The free end of the at least one single-wire preferably has a helical configuration on the first side whilst the free end of the at least one single wire preferably has an undulating configuration on the second side.

For particular preference, the free end of the at least one single-wire is disposed on the first side of the substrate in or adjacent to the through-opening of the second layer, preferably such that, in the region of the through-opening, the single-wire contacts the second layer at least in regions.

The free end of the at least one single-wire on the second side is disposed, in a particularly preferred embodiment of the device according to the invention, in or adjacent to the field or in or adjacent to the cavity in the form of a field, preferably such that the single-wire contacts the first layer at least in regions.

Preferably, the single-wire on the first side of the substrate contacts the first, second and/or third layer on less than or equal to half of its circumference and/or the single-wire on the second side contacts the first and/or fourth layer on less than or equal to half of its circumference.

For particular preference, at least one of the single-wires on the first and/or second side comprises essentially an electrically conductive, preferably ferromagnetic, material, or consists thereof. There are suitable as materials inter alia, metals or metal alloys (e.g. copper, iron, cobalt, nickel, chromium, manganese, silver, gold and alloys hereof) or carbon (e.g. graphite, carbon nanotubes).

Optionally, at least one of the single-wires is coated on the first and/or second side with at least one noble metal, preferably gold at least in regions.

For particular preference, the single-wire is configured in the form of a wire or a strip conductor.

In the device according to the invention, each of the single-wires, i.e. a single electrical conductor, for example a metal wire or a strip conductor, acts as antenna and/or as transmitter of electromagnetic radiation. The received electromagnetic energy is stored in the device, connected to the respective single-wire, for storing electromagnetic energy. Alternatively, e.g. dispensing with a cavity, also the electromagnetic energy to be stored in the device can be input directly on/in the complete device as antenna via the single-wire.

According to the invention, the device can comprise a label which is applied on the cavities after the biological sample has been introduced into the cavity. This label then closes the through-cavity of the third layer and/or the cavity in the form of a field of the fourth layer in a fluid-impermeable and/or moisture-impermeable manner. The biological sample introduced into the cavities can hence be protected from further external influences. The label can be optionally attached on the device before closing the cavities. If the embodiment of the device according to the invention has edges (e.g. credit card format), the label can be attached on one edge of the device.

A few examples of devices according to the invention are given in the following. Identical or similar elements are described therein with identical or similar reference numbers. Individual elements of the subsequent examples are also individually, separate from the overall picture of the respective example, essential to the invention. They can also be combined in any manner with other elements of this type, also from other examples.

BRIEF DESCRIPTION OF THE DRAWINGS

There are shown:

FIGS. 1(1A, 1B, and 1C) a device according to the invention in individual layers.

DESCRIPTION OF PREFERRED EMBODIMENTS

Figure 2:
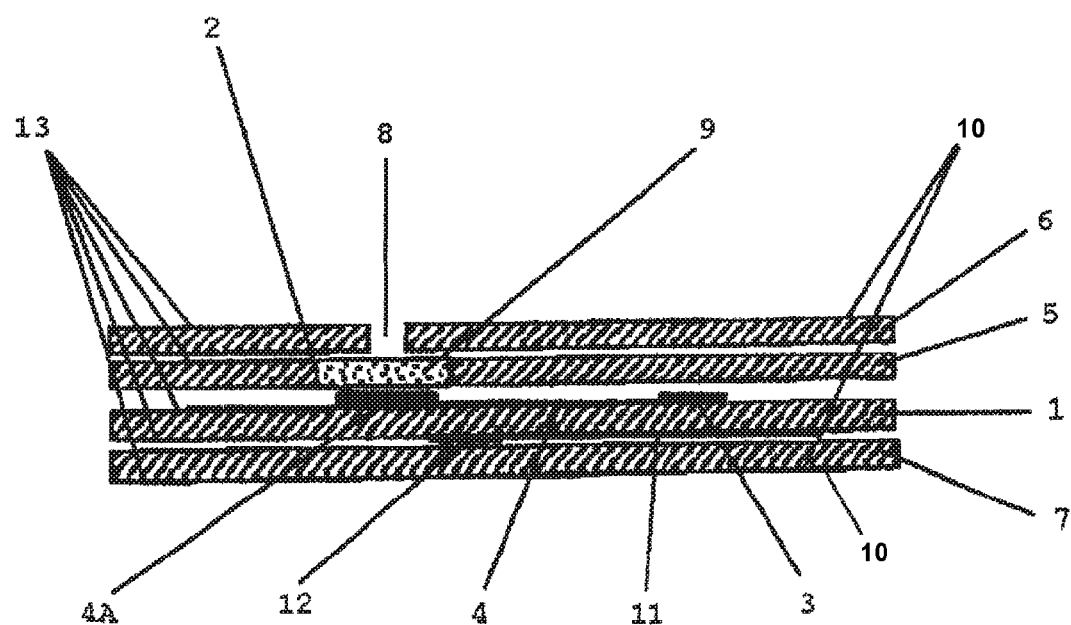
FIG. 2 the construction of a device according to the invention, FIG. 3 the construction of a further device according to the invention, and FIG. 4 the construction of a further device according to the invention.

FIGS. 1(1A, 1B, and 1C) shows a preferred embodiment of the device according to the invention, individual layers being displayed in their sequence. Individual layers 1, 5, 6, 7 of the device are illustrated in side view (A) and in plan view (B). Each layer 1, 5, 6 and 7 has a planar configuration in chip card format (L×W×H=approx. 8.6 cm×approx. 5.4 cm×approx. 0.8 cm).

The first layer 1 is configured as a 0.37 mm thick circuit board made of epoxy resin which comprises, as strip conductors made of copper on the right-hand side, two capacitors 3A, 3B as devices for storing electromagnetic energy and also two single-wires 4A, 4B. The capacitors 3A or 3B are connected respectively on one side to a first end of the single-wires 4A or 4B. The second terminal of the capacitors 3A, 3B is free or insulated. The free second end of the single-wires 4A, 4B has respectively a helical configuration and is disposed on the left-hand side of the layer 1. Furthermore, the first layer 1, on its first side, has a third capacitor 15 as device for storing electromagnetic energy. A further electrical signal can be written into this capacitor.

The second layer 5 consists of polyethylene, has a thickness of 0.20 mm and is glued on the upper side (first side) 5A of the first layer 1, which is provided with the strip conductors 3A, 3B, 4A, 4B. The second layer 5 comprises two circular, through-cavities 2A and 2B which have a diameter in the longitudinal plane of approx. 8.5 mm and are disposed precisely above the free helical end of the single-wires 4A, 4B. The cavities 2A and 2B, on their underside, are sealed by the first layer 1 and are open on their upper side. In the cavities 2A and 2B, respectively one self-adhesive pad 9 which is illustrated separately in FIG. 1 is disposed. The self-adhesive pad 9 consists of a circular, absorbent material and is characterised by a diameter of 8 mm and a thickness of less than 0.20 mm. This pad 9 serves to absorb a body fluid, as mentioned above.

On the second layer 5, a third layer 6 is glued, represented separately here, which third layer is configured as a decorative foil, consists of 0.15 mm thick polyethylene and comprises two through-cavities 8A, 8B in the form of through-holes which are situated respectively precisely in the centre above the cavities 2A and 2B of the second layer 5. The through-holes have a diameter of 2 mm. Apart from the holes, the two cavities 2A and 2B of the second layer 5 are consequently sealed by the decorative foil 6.

On its second side 5B, the first layer 1 has two second arrangements with respectively one field, a single-wire and a device for storing electromagnetic energy, i.e. the second side of the first layer 1 comprises, in the left-hand part, two capacitors 12A, 12B and two undulating single-wires 11A, 11B. The two capacitors 12A, 12B are connected respectively at their one terminal to respectively one of the undulating single-wires 11A, 11B. The free end of the single-wires 11A and 11B extends to the right up to near the edge of the layer 5. The other terminal of the capacitors 12, 12B is free or electrically insulated.

On the second side of the layer 1, in addition a fourth layer 7 is disposed, which is configured as a decorative foil, consists of 0.15 mm thick polyethylene and has an adhesive print and two labelling fields 10A, 10B. The labelling fields 10A, 10B are situated respectively precisely above the single-wires 11A and 11B of the second arrangement. Since all four layers are glued together, a device made of four layers 1, 5, 6 and 7, i.e. a four-layer chip card, is produced as a result. Possible locations for pre-printed writing 13 are illustrated on the fourth layer 7.

FIG. 2 describes the construction of the embodiment, according to the invention, of the device according to FIG. 1 in cross-section. The device has a planar configuration in chip card format (L×W×H)=approx. 8.6 cm×approx. 5.4 cm×approx. 0.8 cm) and has a construction made of the four layers 1, 5, 6, 7. The first layer has a capacitor 3 on the right-hand side as device for storing electromagnetic energy and, in the centre up to the left-hand side, comprises a single-wire 4 made of copper wire. The capacitor 3 is connected at its first terminal to one end of the single-wire 4. The second terminal of the capacitor 3 is free or electrically insulated. The free end of the single-wire 4 (termed here 4A) has a helical configuration and is disposed on the left side of the layer 1.

The second layer 5 comprises a circular, through-cavity 2 which has a diameter in the layer plane of approx. 8.5 mm and is disposed, in the left part of the layer 5, precisely above the helical free end 4A of the single-wire 4. The through-cavity 2 is sealed, in the finished device, on its underside (second side) by layer 1 and is open on its upper side (first side) and hence forms a cavity. In this cavity, a self-adhesive pad 9 is disposed.

The third layer 6 is glued on the second layer and comprises the through-boring 8 which is situated precisely in the centre above the cavity, i.e. above the through-cavity 2 of the second layer 5. The through-boring 8 of the third layer 6, in this example, has a diameter of 2 mm. Apart from the through-boring 8 of the third layer 6, the cavity 2 is sealed by the decorative foil 6. This decorative foil 6 bears various fields 13 with imprints on its upper side. The cavity 2, the capacitor 3 and the strip conductor 4 on the first side of the first layer 1 form a first arrangement.

On the oppositely situated second side of the layer 1, the further layer 7 is glued, which further layer has a printed field 13 and a writing field 10 which can be written upon on its outside. In the region of the writing field 10 and opposite this, an undulating single-wire 11 as strip conductor is disposed on the second side of the second layer 5. The one end of the single-wire 11 is connected to a capacitor 12 which is configured in the region of the left end of the writing field 10 and, opposite this, on the second side of the second layer 5, as strip conductor. The other end of the wire 11 is free and extends in an undulating manner from the capacitor 12 to near to the right outer edge of the layer 5. The field 10, the capacitor 12 and the wire 11 form a second arrangement.

Since all four layers 1, 5, 6 and 7 are glued or welded together, a device made of four layers, i.e. a four-layer chip card, is produced.

FIG. 3 describes the construction of a further embodiment according to the invention of the device according to the invention. Also in FIG. 3, the device has a planar configuration in chip card format, as in FIGS. 1 and 2. It has a construction made of the three layers 1, 5 and 6 which correspond to the layers 1, 5 and 6 of FIG. 2. In this embodiment, the single-wire, starting from the cavity 2 in the layer 1, has a helical course and is connected to a storage device for electromagnetic energy 3. This storage device in FIG. 3 has the form of a finger-shaped capacitor. Both the cavity 2, the single-wire 4 and the capacitor 3 are fitted on one side of the layer 1. On the layer 1, a second layer 5 which has an opening 2' via which the cavity 2 in the layer 1 is accessible is situated. A further decorative foil 6 as third layer is disposed on the layer 2 and likewise has an opening 8 via which the cavity 2 is accessible. In this opening, for example saliva can be applied so that this is introduced into the cavity 2.

FIGS. 4a and 4b show a further embodiment of the device according to the invention. This device has merely one layer 1 which is illustrated in FIG. 4a on its first side (upper side) and in FIG. 4b on its second side (rear-side). In this case of this device, there are fitted the single-wire 4 as antenna and the energy storage device 3 in the form of a finger-shaped capacitor on different sides of the layer 1. They are connected to each other electrically via a through-contact 15.

In the case of this device, a cavity is entirely dispensed with since the corresponding electromagnetic signals can be input for example already in advance in the capacitor without said signals requiring to be input in the single-wire as antenna directly by a biological sample.

The invention claimed is:

1. A device having a planar substrate having a first side and a second side, wherein, on the first side, at least one arrangement is provided, which has at least one single-wire, wherein, on the first side or on the second side, at least one first device for storing electromagnetic energy is provided, one end of the at least one single-wire being connected to the at least one first device for storing the electromagnetic energy, wherein the substrate has at least two layers, the at least one arrangement being disposed at least partially in, on or at a first layer, wherein, on the first side on the first layer, a second layer is disposed, the second layer comprises a through-opening from one side of the second layer to the other side of the second layer, the through-opening being disposed above the free end of the at least one single-wire and forming the first cavity with the first layer, and wherein an absorbent material is disposed in the through-opening of the second layer.

2. A device having a planar substrate having a first side and a second side, wherein, on the first side, at least one first arrangement is provided, which has at least one first single-wire, wherein, on the first side or on the second side, at least one first device for storing electromagnetic energy is provided, one end of the at least one single-wire connected to the at least one first device for storing the electromagnetic energy, and wherein, on the second side of the substrate, at least one second arrangement is provided, the at least one second arrangement has at least one labelling field and at least one second single-wire and wherein on the first side or on the second side, at least one second device for storing electromagnetic energy is provided, one end of the at least one second single-wire being connected to the second device for storing electromagnetic energy and the other end being disposed as a free end in, on or abutting on the labelling field.

3. The device of claim 1, wherein the first layer is a circuit board, the at least one single-wire and the at least first device for storing electromagnetic energy are configured as strip conductors on the circuit board.

4. The device of claim 3, wherein the first layer has an electrically insulating basic material, and wherein the strip conductors comprise an electrically conductive material.

5. A device having a planar substrate having a first side and a second side, wherein, on the first side, at least one arrangement is provided, which has at least one single-wire, wherein, on the first side or on the second side, at least one first device for storing electromagnetic energy is provided, one end of the at least one single-wire connected to the at least one first device for storing the electromagnetic energy, wherein the substrate has at least two layers, the at least one arrangement disposed at least partially in, on or at a first layer, wherein, on the first side on the first layer, a second layer is disposed, the second layer comprises a through-opening from one side of the second layer to the other side of the second layer, the through-opening disposed above the free end of the at least one single-wire and forming the first cavity with the first layer, and wherein the free end of the at least one single-wire, on the first side, is incorporated in the through-opening of the second layer.

6. The device of claim 4, wherein on the first side on the first layer, a second layer is disposed, wherein the second layer comprises at least one of a plastic material, polycarbonate, polyethylene or polyvinyl chloride.

7. The device of claim 1, wherein the through-opening of the second layer is circular and has a diameter of 4.0-15.0 mm, or is angular or oval.

8. The device of claim 4, wherein the electrically insulating basic material is selected from the group consisting of epoxy resin, glass fibre, paper, ceramic, aluminium oxide, polyimide, polytetrafluoroethylene and polyethylene, and wherein the electrically conductive material comprises at least one of a metal, copper, tin, nickel, gold or platinum.

9. The device of claim 1, wherein the absorbent material is configured as a circular, absorbent pad.

10. The device of claim 1, wherein the absorbent material is configured to adsorb body fluids.

11. The device of claim 1, wherein on the first side on the first layer, a second layer is disposed, wherein a third layer is disposed on a side of the first layer or the second layer orientated away from the first layer, the third layer comprises a through-opening from a first side of the third layer to a second side of the third layer.

12. The device of claim 11, wherein the third layer contacts the second layer such that the through-opening of the third layer is situated above a through-opening of the second layer.

13. The device of claim 11, wherein the diameter of the through-opening in the third layer is smaller than the diameter of a through-opening in the second layer.

14. The device of claim 13, wherein the through-opening of the third layer is circular and has a diameter of 0.5-3.5 mm, 1.0-3.0 mm, or 1.5-2.5 mm, or is oval or rectangular.

15. The device of claim 14, wherein the third layer comprises plastic material comprising or consisting of polycarbonate, polyethylene or polyvinyl chloride.

16. The device of claim 1, wherein the at least one arrangement on the first side of the substrate is at least one first arrangement, wherein the at least one single-wire is at least one first single wire, and wherein, on the second side of the substrate, at least one second arrangement is provided, the at least one second arrangement has at least one labelling field and at least one second single-wire and in that, on the first side or on the second side, at least one second device for storing electromagnetic energy is provided, one end of the at least one second single-wire being connected to the second device for storing electromagnetic energy and the other end being disposed as free end in, on or abutting on the labelling field.

17. The device of claim 16, wherein the substrate has at least two layers including a first layer, wherein the at least one second arrangement is disposed in, on or abutting on a second side of the first layer.

18. The device of claim 11, wherein, on the second side of the first layer, a fourth layer is disposed, which fourth layer has at least one labelling field or at least one through-cavity in the form of a labelling field.

19. The device of claim 18, wherein the fourth layer comprises plastic material comprising or consisting of polycarbonate, polyethylene or polyvinyl chloride.

20. The device of claim 18 or 19, wherein the labelling field or the through-cavity in the form of a labelling field is rectangular, circular, or oval.

21. The device of claim 18 or 19, wherein the at least one labelling field or the at least one cavity in the form of a labelling field has a material which can be written upon.

22. The device of claim 21, wherein the material which can be written upon is configured to adsorb and/or to adsorb solid and/or liquid writing material.

23. The device of claim 1, wherein the at least two layers of the substrate are extensively round, oval or rectangular.

24. The device of claim 1, wherein the at least two layers of the substrate are configured in card format.

25. The device of claim 16, wherein a third device for storing electromagnetic energy is disposed on, in or abutting on the substrate.

26. The device of claim 25, wherein at least one, several or all of the devices for storing electromagnetic energy are a capacitor or have a capacitor.

27. The device of claim 1, wherein the device, on the first side, has one, two or three arrangements.

28. The device of claim 16, wherein the device, on the second side, has one, two, or three second arrangements.

29. The device of claim 1, wherein the free end of the at least one single-wire has a helical configuration on the first side.

30. The device of claim 16, wherein the free end of the at least one second single-wire has an undulating configuration on the second side.

31. The device of claim 1, wherein the free end of the at least one single-wire, on the first side, is incorporated in the through-opening of the second layer.

32. The device of claim 17, wherein the free end of the at least one single-wire, on the second side, is incorporated in the labelling field or in the cavity in the form of a labelling field such that the at least one single-wire contacts the first layer at least in regions.

33. The device of claim 30, wherein the at least one first single-wire, on the first side, contacts a first layer, a second layer and/or a third layer of the substrate on less than or equal to half of the circumference of the at least one first single-wire, and/or the at least one second single-wire, on the second side, contacts the first layer and/or a fourth layer of the substrate on less than or equal to half of the circumference of the at least one second single-wire.

34. The device of claim 16, wherein at least one of the at least one first single-wire or the at least one second single-wire
   a) comprises or consists of an essentially electrically conductive material; and/or
   b) is coated with at least one noble metal, at least in regions.

35. The device of claim 1, wherein the at least one arrangement has at least one first cavity.

36. The device of claim 35, wherein the other end of the at least one single-wire is disposed as free end in, below or abutting on the first cavity.

37. The device of claim 24, wherein the at least two layers of the substrate have the dimensions length×width×height of 2-14 cm×2-10 cm×0.05-0.60 mm, or of 8-9 cm×5-6 cm×0.15-0.40 mm.

38. The device of claim 31, wherein the free end of the at least one single-wire, on the first side, is incorporated in the through-opening of the second layer such that, in the region of the through-opening, the at least one single-wire contacts the first and/or second layer at least in regions.

39. The device of claim 5, wherein in the region of the through-opening, the at least one single-wire contacts the first and/or second layer at least in regions.

40. The device of claim 34, wherein at least one of the at least one first single-wire or the at least one second single-wire
   a) comprises or consists of a ferromagnetic material; and/or
   b) is coated with at least gold, at least in regions.

41. The device of claim 7, wherein the through-opening of the second layer is circular and has a diameter of 6.0-12.0 mm or of 8.0-9.0 mm.

42. The device of claim 10, wherein the absorbent material is configured to adsorb at least one of blood or saliva.

43. The device of claim 9, wherein the circular, absorbent pad has a diameter in a plane of the second layer of 4.0-15.0 mm, 6.0-12.0 mm, or 8.0-9.0 mm.

44. The device of claim 11, wherein the third layer is configured as a self-adhesive decorative foil.

45. The device of claim 12, wherein the third layer contacts the second layer such that the through-opening of the third layer is situated in the centre of the through-opening of the second layer.

46. The device of claim 18, wherein the fourth layer is configured as a self-adhesive decorative foil.

47. The device of claim 20, wherein the labelling field is rectangular having the dimensions length×width of 2-7 cm×0.5-2 cm, or 4-6 cm×0.8-1.5 cm.

* * * * *